United States Patent
Barnes et al.

(10) Patent No.: US 10,997,566 B2
(45) Date of Patent: May 4, 2021

(54) EXERCISE BEHAVIOR PREDICTION

(71) Applicant: CarePredict, Inc., Plantation, FL (US)

(72) Inventors: Ronald A. Barnes, San Antonio, TX (US); Jason A. Beens, Helotes, TX (US); David P. Elam, Jr., San Antonio, TX (US); Bennett L. Ibey, San Antonio, TX (US); Gerald J. Wilmink, San Antonio, TX (US)

(73) Assignee: CarePredict, Inc., Plantation, FL (US)

( * ) Notice: Subject to any disclaimer, the term of this patent is extended or adjusted under 35 U.S.C. 154(b) by 945 days.

(21) Appl. No.: 15/592,433

(22) Filed: May 11, 2017

(65) Prior Publication Data

US 2017/0249599 A1    Aug. 31, 2017

Related U.S. Application Data

(63) Continuation of application No. 14/556,191, filed on Nov. 30, 2014, now Pat. No. 9,691,023.

(51) Int. Cl.
*G06N 5/02* (2006.01)
*G06N 5/04* (2006.01)
*G06Q 10/10* (2012.01)
*G09B 7/02* (2006.01)

(52) U.S. Cl.
CPC .......... *G06Q 10/1095* (2013.01); *G06N 5/02* (2013.01); *G06N 5/04* (2013.01); *G09B 7/02* (2013.01)

(58) Field of Classification Search
CPC ......... G06N 5/02; G06N 5/04; G06Q 10/1095
See application file for complete search history.

(56) References Cited

U.S. PATENT DOCUMENTS

| | | | |
|---|---|---|---|
| 8,812,264 B2 | 8/2014 | Runkle | |
| 9,116,986 B1* | 8/2015 | Jackson | G06F 16/36 |
| 2007/0135264 A1 | 6/2007 | Rosenberg | |
| 2010/0056341 A1 | 3/2010 | Ellis et al. | |
| 2013/0044042 A1 | 2/2013 | Olsson et al. | |
| 2013/0116092 A1* | 5/2013 | Martinez | A63B 24/0087 482/9 |
| 2013/0325358 A1 | 12/2013 | Oshima et al. | |
| 2014/0195018 A1 | 7/2014 | Kang et al. | |
| 2014/0214903 A1 | 7/2014 | Stivoric et al. | |

(Continued)

FOREIGN PATENT DOCUMENTS

| | | |
|---|---|---|
| WO | WO/2013/002568 | 1/2013 |
| WO | WO/2014/053538 A1 | 4/2014 |

*Primary Examiner* — Hal Schnee
(74) *Attorney, Agent, or Firm* — DLA Piper LLP (US)

(57) ABSTRACT

Methods, apparatuses, and computer readable mediums for exercise behavior prediction are provided. In a particular embodiment, the prediction evaluation controller is configured to generate an exercise activity pattern based on correlations between scheduling of a user's historical non-exercise events and the user's historical exercise events. In the particular embodiment, the prediction evaluation controller is also configured to generate, based on the generated exercise activity pattern, by the prediction evaluation controller, a future exercise event to correspond with a future non-exercise event scheduled on the user's calendar. In the particular embodiment, the prediction evaluation controller is also configured to provide an indication of the generated future exercise event.

20 Claims, 9 Drawing Sheets

(56) References Cited

U.S. PATENT DOCUMENTS

2014/0273925 A1* 9/2014 Burgett ............. H04M 1/72558
　　　　　　　　　　　　　　　　　　　455/405
2015/0081210 A1　　3/2015 Yeh et al.
2015/0364057 A1* 12/2015 Catani ................ G09B 19/0092
　　　　　　　　　　　　　　　　　　　434/127

* cited by examiner

Figure 1:
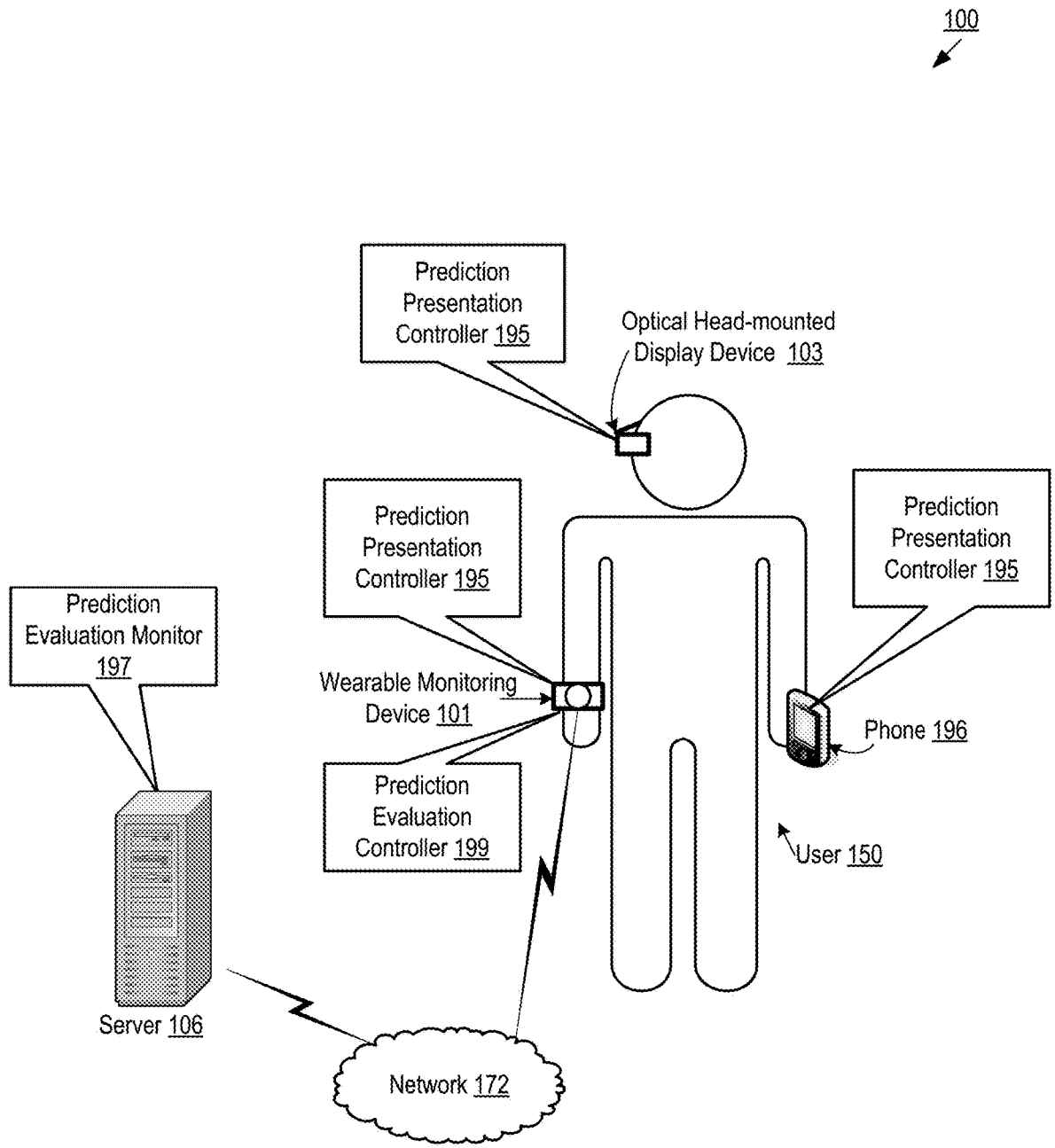

EXERCISE BEHAVIOR PREDICTION
>
> ## CROSS-REFERENCE TO RELATED APPLICATION
>
> This application is a continuation application of and claims priority from U.S. patent application Ser. No. 14/556,191, filed Nov. 30, 2014.
>
> ## BACKGROUND
>
> ### Field of the Invention
>
> The field of the invention is data processing, or, more specifically, methods, apparatuses, and computer readable mediums for exercise behavior prediction.
>
> ### Description of Related Art
>
> The health benefits of regular exercise and physical activity are well documented. A hectic schedule filled with non-exercise activities may impair a person's ability to schedule a time to exercise, much less to actually select an exercise activity for the scheduled time.
>
> ## SUMMARY
>
> Methods, apparatuses, and computer readable mediums for exercise behavior prediction are provided. In a particular embodiment, the prediction evaluation controller is configured to generate an exercise activity pattern based on correlations between scheduling of a user's historical non-exercise events and the user's historical exercise events. In the particular embodiment, the prediction evaluation controller is also configured to generate, based on the generated exercise activity pattern a future exercise event to correspond with a future non-exercise event scheduled on the user's calendar. In the particular embodiment, the prediction evaluation controller is also configured to provide an indication of the generated future exercise event.
>
> The foregoing and other objects, features and advantages of the present disclosure will become apparent after review of the entire application, including the following sections: Brief Description of the Drawings, Detailed Description, and the Claims.
>
> ## BRIEF DESCRIPTION OF THE DRAWINGS
>
> FIG. 1 sets forth a diagram of an illustrative embodiment of an apparatus for exercise behavior prediction.
>
> FIG. 2 sets forth a block diagram of another illustrative embodiment of an apparatus for exercise behavior prediction.
>
> FIG. 3 sets forth a diagram illustrating an example graphical user interface of a calendar that utilizes an embodiment of exercise behavior prediction.
>
> FIG. 4 sets forth a flow chart illustrating an example embodiment of a method for exercise behavior prediction.
>
> FIG. 5 sets forth a flow chart illustrating another example embodiment of a method for exercise behavior prediction.
>
> FIG. 6 sets forth a flow chart illustrating another example embodiment of a method for exercise behavior prediction.
>
> FIG. 7 sets forth a flow chart illustrating another example embodiment of a method for exercise behavior prediction.
>
> FIG. 8 sets forth a flow chart illustrating another example embodiment of a method for exercise behavior prediction.
>
> FIG. 9 sets forth a data flow diagram illustrating a manufacturing process of a device configured for exercise behavior prediction.
>
> ## DETAILED DESCRIPTION
>
> FIG. 1 sets forth a diagram of an illustrative embodiment of an apparatus (100) for exercise behavior prediction (150). In the example of FIG. 1, the apparatus (100) includes a wearable monitoring device (101), an optical head-mounted display device (103), a phone (196), and a server (106).
>
> A wearable monitoring device is any device that is wearable and includes automated computing machinery for monitoring a user. Non-limiting examples of wearable monitoring devices include smart wristwatches, bracelets, straps, pendants, and any other forms of wearable devices capable of monitoring a user. In the example of FIG. 1, the wearable monitoring device (101) is a smart strap attached to the wrist of the user (150). Readers of skill in the art will recognize that wearable monitoring devices may be placed on any number of locations on a user.
>
> As part of 'monitoring' a user, a wearable monitoring device may be configured to utilize data from one or more sensors that are either coupled to the wearable monitoring device or are part of the wearable monitoring device. Non-limiting examples of the types of sensors that may be available to a wearable monitoring device include a hydration sensor, a heart rate monitor, an ECG monitor, a pulse oximeter, a thermometer, an electromyography (EMG) sensor, an accelerometer, a gyroscope, a Global Positioning System (GPS) location sensor, an environmental condition sensor, and many other types of sensors that would be useful for monitoring a user.
>
> To acquire data from these sensors, a wearable monitoring device may include data acquisition (DAQ) hardware for periodically polling or receiving data from one or more of the sensors available to the wearable monitoring device. For example, circuitry within the wearable monitoring device may monitor the existence and strength of a signal from a sensor and process any signals received from the sensor. The wearable monitoring device (101) may also include circuitry for processing the sensor data. For example, the wearable monitoring device (101) may include circuitry for converting sensor data to another data form, such as physiological data and environmental condition data. That is, the wearable monitoring device (101) of FIG. 1 may include the computing components necessary to receive, process, and transform sensor data into a type of data that is usable in a process for exercise behavior prediction.
>
> In the example of FIG. 1, the wearable monitoring device (101) includes a prediction evaluation controller (199) comprised of automated computing machinery configured for exercise behavior prediction of the user (150). As part of the process of exercise behavior prediction, the prediction evaluation controller (199) is configured to generate an exercise activity pattern based on correlations between scheduling of a user's historical non-exercise events and the user's historical exercise events. A historical exercise event is a calendar event that indicates the user performed or at least was scheduled to perform an exercise activity at a particular time before the user's current time. Non-limiting examples of exercise activities include running, walking, jogging, bicycling, swimming, jumping rope, weightlifting, pushups, curl ups, yoga, elliptical moving, climbing stairs, any many other types of physical positioning that may be considered by one of skill in the art to constitute exercising. A historical exercise event may include data associated with the performance of the exercise activity. Non-limiting examples of data that may be associated with the performance of the exercise activity and that may be included in the historical exercise event include a start time of the exercise activity, a location of the exercise activity, other attendees of the exercise activity, a duration of the exercise activity, preset goals of the exercise activity, and any other information that may be useful for evaluating the historical exercise event. This data may be entered by the user or may be automatically generated based on sensor data. As part of automatically generating the data, a wearable monitoring device attached to a user may determine when the user is performing an exercise activity and may use sensor data to generate data associated with the exercise activity. For example, the wearable monitoring device (101) may determine the length of time a user is performing an exercise activity, a location the exercise activity was performed, and a physiological state of the user while the user performed the exercise activity.

A historical non-exercise event is a calendar event that indicates the user performed or at least was scheduled to perform a non-exercise activity at a particular time before the user's current time. Non-limiting examples of non-exercise activities include attending meetings, driving, flying, making telephone calls, sleeping, showering, and any other type of activity that would not be considered by one of skill in the art to constitute exercising. A historical non-exercise event may include data associated with the non-exercise activity. Non-limiting examples of data that may be associated with the performance of the non-exercise activity and that may be included in the historical non-exercise event include a start time of the non-exercise activity, a location of the non-exercise activity, other attendees of the non-exercise activity, a duration of the non-exercise activity, a type or classification of the non-exercise activity, and any other information that may be useful for evaluating the historical non-exercise event. This data may be entered by the user or may be automatically generated based on sensor data. As part of automatically generating the data, a wearable monitoring device attached to a user may determine when the user is performing a non-exercise activity and may use sensor data to generate data associated with the non-exercise activity. For example, a wearable monitoring device may determine the length of time a user is performing the non-exercise activity and the location the non-exercise activity was performed.

In a particular embodiment, to generate the data associated with the exercise event, the wearable monitoring device (101) may: determine that the user is performing an exercise activity; determine the type of exercise activity; create an exercise event in the user's calendar indicating that the user is performing an exercise activity at a particular time; and store any data collected, generated, or associated with the performance of that exercise activity. Determining that a user is performing a non-exercise activity may also be possible by examining the user's location, the user's current time, and historical calendar information to predict what non-exercise activity the user is doing. For example, a user may have a staff meeting scheduled every day at 5 P.M. at a particular location. Continuing with this example, the wearable monitoring device may schedule or prompt the user to add a staff meeting to the user's calendar in response to detecting that the user is at the particular location at 5 P.M. on a day where the staff meeting is not scheduled.

An exercise activity pattern is an indication of a repeated scheduling sequence of exercise events and non-exercise events on a user's calendar. In a particular embodiment, an exercise activity pattern consists of a rule set that indicates the repeated scheduling sequence of some combination of an exercise event and a non-exercise event. Correlations between a particular exercise event and a non-exercise event may be indicated by a variety of factors, including but not limited to: a duration of time between a non-exercise event and an exercise event; a relationship between a type or classification of a non-exercise event and an exercise event; a type of exercise activity performed during an exercise event in relation to a non-exercise event; a location of a non-exercise event and an exercise event; attendees of an exercise event or a non-exercise event; and many types of information that may be useful to indicate a pattern between an exercise event and a non-exercise event.

In summary, generating an exercise activity pattern based on correlations between scheduling of a user's historical non-exercise events and the user's historical exercise events may be carried out by retrieving a user's calendar data; examining the user's calendar data to identify repeating sequences of exercise events and non-exercise events; and creating one or more rule sets specifying a relationship between an exercise event and a non-exercise event.

For example, an exercise activity pattern may include a rule set and data that indicates that an exercise event historically precedes a non-exercise event by a particular duration or range of time. In this example, the exercise activity pattern may indicate that a user historically goes for a run two hours before going to the airport. Another example exercise activity pattern may include a rule set that indicates an exercise event follows a particular type of non-exercise event, such as an investor meeting.

As part of the process for exercise behavior prediction, the prediction evaluation controller (199) is also configured to generate, based on the generated exercise activity pattern, a future exercise event to correspond with a future non-exercise event scheduled on the user's calendar. A future non-exercise event is a calendar event that indicates the user is scheduled to perform a non-exercise activity at a particular time after the current time. A future non-exercise event may include data associated with the non-exercise activity. Non-limiting examples of data that may be associated with the performance of the future non-exercise activity and that may be included in the future non-exercise event include a start time of the future non-exercise activity, a location of the future non-exercise activity, anticipated attendees of the future non-exercise activity, a scheduled duration of the non-exercise activity, a type or classification of the non-exercise activity, and any other information that may be useful for evaluating the future non-exercise event.

A future exercise event is a calendar event that indicates the user is scheduled to perform an exercise activity at a particular time after the current time. A future exercise event may include data associated with an exercise activity scheduled to be performed during the future exercise event. Non-limiting examples of data that may be associated with the future exercise activity scheduled to be performed include a start time of the future exercise activity, a location of the future exercise activity, anticipated attendees of the future exercise activity, a scheduled duration of the future exercise activity, preset goals of the future exercise activity, and any other information that may be useful for evaluating or scheduling the future exercise event. Generating, based on the generated exercise activity pattern, a future exercise event to correspond with a future non-exercise event scheduled on the user's calendar may be carried out by identifying the future non-exercise event; utilizing the generated exercise activity pattern to identify a candidate future exercise event; and determine whether the user's calendar includes a future exercise event that corresponds with the candidate future exercise event. If the prediction evaluation controller (199) determines that the user's calendar does not include a future exercise event that corresponds with the candidate future exercise event, the prediction evaluation controller (199) may use the candidate future exercise event as the generated future exercise event.

As part of the process for exercise behavior prediction, the prediction evaluation controller (199) is also configured to provide an indication of the generated future exercise event. Providing an indication of the generated future exercise event may be carried out by communicating the indication of the generated future exercise event to the user. Providing an indication of the generated future exercise event may also include communicating an explanation for why the generated future exercise event is being indicated. For example, the prediction evaluation controller may transmit an audio message to the user via a speaker or audio output on the wearable monitoring device. In this example, the audio message may identify information associated with the generated future exercise event along with an explanation for why the generated future exercise event is being recommended. Non-limiting examples of explanations for why the generated future exercise event is being recommended include: "you typically exercise after an investor meeting"; "you like to go for a run before going out of town"; and "typically, you go for a walk before staff meetings, would you like to schedule a walk after before your staff meeting tomorrow?".

As another example, the prediction evaluation controller (199) may transmit a visual output to a screen of the wearable monitoring device (101). In this example, the visual output may display the generated future exercise event along with an explanation for why the generated future exercise event is being indicated. Examples of visual output may include a displayed message, an animated avatar performing the generated future exercise event, and many others as will occur to Readers of skill in the art.

In a particular embodiment, providing an indication of the generated future exercise event may include transmitting the indication of the future exercise event to a prediction presentation controller (195). A prediction presentation controller includes automated computing machinery configured to receive the indication of the generated future exercise event and to present the indication of the generated future exercise event to a user. In the example of FIG. 1, the phone (196) and the optical head-mounted display device (103) both include the prediction presentation controller (195). The phone (196) and the optical head-mounted display device (103) may include visual and audio outputs for providing the indication of the generated future exercise event to the user (150). The wearable monitoring device (101) of FIG. 1 also includes the prediction presentation controller (195). However, Readers of skill in the art will realize that the prediction presentation controller (195) and the prediction evaluation controller (199) need not be incorporated into the same device.

The prediction evaluation controller (199) may also be configured to provide an indication of the generated future exercise event to another device. For example, the prediction evaluation controller (199) may provide the indication of the generated future exercise event to a server (106) via a network (172). The server (106) includes a prediction evaluation monitor (197). The prediction evaluation monitor (197) may include automated computing machinery configured to receive the indication of the generated future exercise event and the generated exercise activity patterns. The recommendation evaluation monitor (197) may also be configured to act as a database repository for that stores physiological data, environmental condition data, and any other type of data that the prediction evaluation controller (199) may utilize to generate and provide a future exercise event to a user. The prediction evaluation monitor (197) may be configured to provide this stored data to the prediction evaluation controller (199). The prediction evaluation monitor (197) may also be configured to act as a central repository for multiple users so that users can share performance results, physiological data, sensed data, environmental condition data, indications of the future exercise events, and explanations for the indications of the future exercise events. For example, a user of the wearable monitoring device (101) may forward an indication of a future exercise event to another user. The other user may use the indication of the future exercise event to schedule the future exercise event on the other user's calendar.

Figure 2:
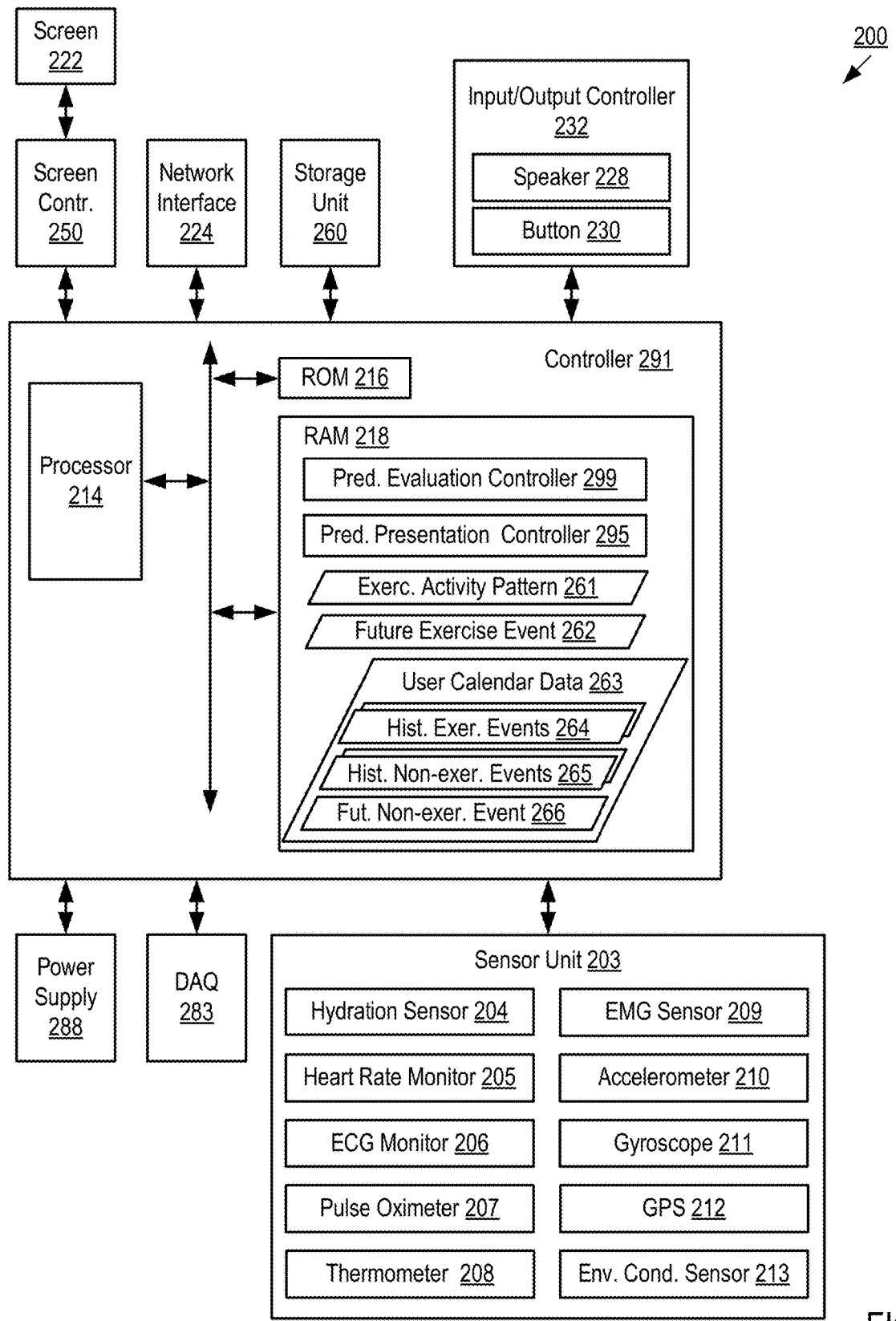

Referring to FIG. 2, an illustrative apparatus (200) for exercise behavior prediction is shown. The apparatus (200) includes a controller (291) that includes a processor (214), read only memory (ROM) (216), random access memory (RAM) (218). The RAM (218) includes a prediction evaluation controller (299) and a prediction presentation controller (295). Although, in the example of FIG. 2, the prediction evaluation controller (299) and the prediction presentation controller (295) are included in RAM (218), Readers of skill in the art will recognize that the prediction evaluation controller (299) and the prediction presentation controller (295) may be included in other storage locations, such as the ROM (216) and an external storage unit (260), which is coupled for data communications with the controller (291).

In the example of FIG. 2, the apparatus (200) also includes a power supply (288), a screen (222), a screen controller (250), a network interface (224), an input/output controller (232) having a speaker (228) and a button (230), a data acquisition processing unit (DAQ) (283), and a sensor unit (203). The sensor unit (203) of FIG. 2 includes sensors for generating, capturing, and transmitting motion data. In the example of FIG. 2, the sensor unit (203) includes an accelerometer (210), a gyroscope (211), and a global positioning system unit (212).

An accelerometer measures proper acceleration, which is the acceleration it experiences relative to freefall and is the acceleration felt by people and objects. Put another way, at any point in spacetime the equivalence principle guarantees the existence of a local inertial frame, and an accelerometer measures the acceleration relative to that frame. Such accelerations are popularly measured in terms of g-force. Conceptually, an accelerometer behaves as a damped mass on a spring. When the accelerometer experiences an acceleration, the mass is displaced to the point that the spring is able to accelerate the mass at the same rate as the casing. The displacement is then measured to give the acceleration. Modern accelerometers are often small micro electro-mechanical systems (MEMS), and are indeed the simplest MEMS devices possible, consisting of little more than a cantilever beam with a proof mass (also known as seismic mass). Damping results from the residual gas sealed in the device. As long as the Q-factor is not too low, damping does not result in a lower sensitivity. Most micromechanical accelerometers operate in-plane, that is, they are designed to be sensitive only to a direction in the plane of the die. By integrating two devices perpendicularly on a single die a two-axis accelerometer can be made. By adding another out-of-plane device three axes can be measured. Such a combination may have much lower misalignment error than three discrete models combined after packaging. Micromechanical accelerometers are available in a wide variety of measuring ranges, reaching up to thousands of g's.

A gyroscope is a device for measuring or maintaining orientation, based on the principles of angular momentum. Mechanical gyroscopes typically comprise a spinning wheel or disc in which the axle is free to assume any orientation. Although the orientation of the spin axis changes in response to an external torque, the amount of change and the direction of the change is less and in a different direction than it would be if the disk were not spinning. When mounted in a gimbal (which minimizes external torque), the orientation of the spin axis remains nearly fixed, regardless of the mounting platform's motion. Gyroscopes based on other operating principles also exist, such as the electronic, microchip-packaged MEMS gyroscope devices found in consumer electronic devices, solid-state ring lasers, fibre optic gyroscopes, and the extremely sensitive quantum gyroscope. A MEMS gyroscope takes the idea of the Foucault pendulum and uses a vibrating element, known as a MEMS (Micro Electro-Mechanical System). The integration of the gyroscope has allowed for more accurate recognition of movement within a 3D space than the previous lone accelerometer within a number of smartphones. Gyroscopes in consumer electronics are frequently combined with accelerometers (acceleration sensors) for more robust direction- and motion-sensing.

The Global Positioning System (GPS) is a space-based satellite navigation system that provides location and time information in all weather conditions, anywhere on or near the Earth where there is an unobstructed line of sight to four or more GPS satellites. In general, GPS receivers are composed of an antenna, tuned to the frequencies transmitted by the satellites, receiver-processors, and a highly stable clock (often a crystal oscillator).

The sensor unit (203) of FIG. 2 also includes a sensor (213) for generating, capturing, and transmitting environmental condition data. Environmental condition data may include any indications of the environment of the user. In a particular embodiment, environmental condition data may indicate weather conditions, such as humidity level, precipitation measurements, cloud coverage, and temperature. Environmental condition data may also indicate whether the user is inside or outside. For example, a user may provide input to the wearable monitoring device indicating that the user is indoors. In another embodiment, environmental condition data may be measured by the wearable monitoring device. For example, the wearable monitoring device may include a sensor that monitors humidity level or temperature surrounding the wearable monitoring device. In another embodiment, the wearable monitoring device may use one or more network interfaces to receive indications of environmental conditions, such as from a weather indication application, or from a local environmental condition indication device, such as a networked humidity and temperature sensor.

The sensor unit (203) of FIG. 2 also includes sensors for generating, capturing, and transmitting physiological data. In the example of FIG. 2, the sensor unit (203) includes a hydration sensor (204), a heart rate monitor (205), an electrocardiograph (ECG) monitor (206), a pulse oximeter (207), a thermometer (208), and an electromyograph (209) for performing electromyography (EMG).

A hydration sensor may be any type of sensor capable of measuring a hydration level of a person. Measuring a hydration level of a person may be performed by a variety of methods via a variety of systems, including but not limited to measuring transepidermal water loss (TWL) with a skin hydration probe. TWL is defined as the measurement of the quantity of water that passes from inside a body through the epidermal layer (skin) to the surrounding atmosphere via diffusion and evaporation processes.

A heart rate monitor (HRM) typically functions by detecting an electrical signal that is transmitted through the heart muscle as the heart contracts. This electrical activity can be detected through the skin. An ECG monitor also generates an activity pattern based on electrical activity of the heart. On the ECG, instantaneous heart rate is typically calculated using the R wave-to-R wave (RR) interval and multiplying/dividing in order to derive heart rate in heartbeats/min.

A pulse oximeter is a medical device that indirectly monitors the oxygen saturation of a user's blood (as opposed to measuring oxygen saturation directly through a blood sample) and changes in blood volume in the skin, producing a photoplethysmogram. A typical pulse oximeter utilizes an electronic processor and a pair of small light-emitting diodes (LEDs) facing a photodiode through a translucent part of the patient's body, usually a fingertip or an earlobe. Typically one LED is red, with wavelength of 660 nm, and the other is infrared with a wavelength of 940 nm. Absorption of light at these wavelengths differs significantly between blood loaded with oxygen and blood lacking oxygen. Oxygenated hemoglobin absorbs more infrared light and allows more red light to pass through. Deoxygenated hemoglobin allows more infrared light to pass through and absorbs more red light. The LEDs flash about thirty times per second which allows the photodiode to respond to the red and infrared light separately. The amount of light that is transmitted (in other words, that is not absorbed) is measured, and separate normalized signals are produced for each wavelength. These signals fluctuate in time because the amount of arterial blood that is present increases (literally pulses) with each heartbeat. By subtracting the minimum transmitted light from the peak transmitted light in each wavelength, the effects of other tissues is corrected for. The ratio of the red light measurement to the infrared light measurement is then calculated by the processor (which represents the ratio of oxygenated hemoglobin to deoxygenated hemoglobin), and this ratio is then converted to SpO2 by the processor via a lookup table.

A thermometer is a device that measures temperature or a temperature gradient. A thermistor is an example of a type of thermometer that may be used to measure temperature. A thermistor is a type of resistor whose resistance varies significantly with temperature, more so than in standard resistors. Thermistors are widely used as inrush current limiters, temperature sensors, self-resetting overcurrent protectors, and self-regulating heating elements.

An electromyograph detects the electrical potential generated by muscle cells when these cells are electrically or neurologically activated. The signals can be analyzed to detect medical abnormalities, activation level, or recruitment order or to analyze the biomechanics of human or animal movement.

The data acquisition (DAQ) hardware (283) is configured for periodically polling or receiving data from one or more sensors. For example, circuitry within the DAQ (283) may monitor the existence and strength of a signal from a sensor and process any signals received the sensor. The DAQ (283) may also include circuitry for processing the sensor data. For example, the DAQ (283) may include circuitry for conversion of sensor data to another data form, such as motion data, physiological data, or environmental condition data. That is, the DAQ (283) of FIG. 2 may include the computing components necessary to receive, process, and transform sensor data into a type of data that is usable in a process for exercise behavior prediction.

The prediction evaluation controller (299) comprises automated computing machinery configured for exercise behavior prediction of a user. Specifically, the prediction evaluation controller (299) is configured to generate an exercise activity pattern (261) based on correlations between scheduling of a user's historical non-exercise events (265) and the user's historical exercise events (264). In the example of FIG. 2, the user's historical non-exercise events (265) and the user's historical exercise events (264) are included in user calendar data (263) stored in RAM (218). The prediction evaluation controller (299) is also configured to generate, based on the generated exercise activity pattern (261), a future exercise event (262) to correspond with a future non-exercise event (266) scheduled on the user's calendar. In the example of FIG. 2, the prediction evaluation controller is also configured to provide an indication of the generated future exercise event (262).

The prediction presentation controller (295) comprises automated computing machinery configured for exercise behavior prediction of a user. Specifically, the prediction presentation controller (295) is configured to receive the indication of the generated future exercise event (262) and to present the indication of the generated future exercise event to the user. In the example of FIG. 2, the prediction presentation controller (295) may provide the indication of the generated future exercise event by: generating and transmitting visual output that is used to display a message within a graphical user interface displayed on the screen (222); and generating and transmitting audio output that is used to play audio over on the speaker (228).

The controller (291) is also coupled to a network interface (224), such as an Ethernet port, modem port or other network port adapter. The network interface (224) is adapted to connect to a network and to send data to a prediction presentation controller or a prediction evaluation monitor located on a separate device. The network may include one or a combination of any type of network such as LAN, WAN, WLAN, public switched telephone network, GSM, or otherwise.

In a particular embodiment, the power supply (288) may include circuitry used for inductive charging. Inductive charging (also known as "wireless charging") uses an electromagnetic field to transfer energy between two objects. This is usually done with a charging station. Energy is sent through an inductive coupling to an electrical device, which can then use that energy to charge batteries or run the device. Induction chargers typically use an induction coil to create an alternating electromagnetic field from within a charging base station, and a second induction coil in the portable device takes power from the electromagnetic field and converts it back into electrical current to charge the battery. The two induction coils in proximity combine to form an electrical transformer. Greater distances between sender and receiver coils can be achieved when the inductive charging system uses resonant inductive coupling. Recent improvements to this resonant system include using a movable transmission coil (i.e., mounted on an elevating platform or arm), and the use of advanced materials for the receiver coil made of silver plated copper or sometimes aluminum to minimize weight and decrease resistance due to the skin effect.

Figure 3:
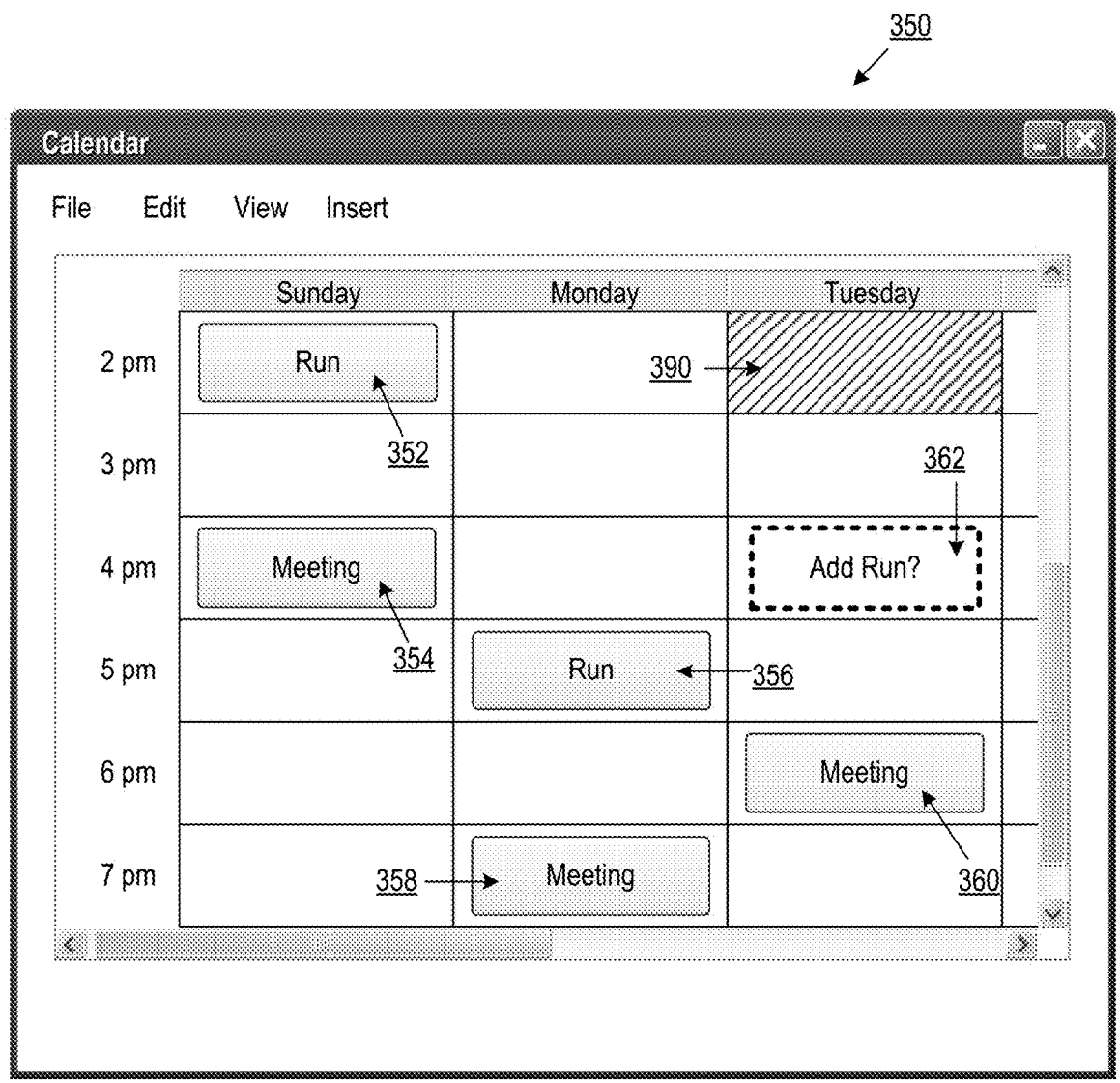

For further explanation, FIG. 3 sets forth a diagram illustrating an example graphical user interface (GUI) (350) of a calendar that utilizes an embodiment of exercise behavior prediction. In the example of FIG. 3, the shaded area (390) indicates that the current time is 2 P.M. on Tuesday. The events (both non-exercise and exercise) that were scheduled on Sunday and Monday are considered historical. For example, the GUI (350) includes a first historical exercise event (352) scheduled at 2 P.M. on Sunday followed by a first historical non-exercise event (354) scheduled at 4 P.M. On Monday, the GUI (350) has scheduled a second historical exercise event (356) at 5 P.M. followed by a second historical non-exercise event (358) at 7 P.M. The GUI (350) of FIG. 3 also includes a future non-exercise event (360) scheduled at 6 P.M. on Tuesday.

According to various embodiments, a prediction evaluation controller may generate an exercise activity pattern based on correlations between scheduling of a user's historical non-exercise events (354, 358) and the user's historical exercise events (352, 356). As part of generating an exercise activity pattern, a prediction evaluation controller may retrieve user calendar data; examine the user calendar data to identify repeating sequences of exercise events and non-exercise events; and create one or more rule sets specifying a relationship between an exercise event and a non-exercise event. In the example of FIG. 3, the prediction evaluation controller may generate an exercise activity pattern that indicates that the user historically goes for a run two hours before a meeting.

After generating the exercise activity pattern, the prediction evaluation controller may generate, based on the generated exercise activity pattern, a future exercise event (362) to correspond with a future non-exercise event (360) scheduled on the user's calendar. In the example of FIG. 3, the prediction evaluation controller may identify the future non-exercise event (360); determine that the future non-exercise event (360) does not have an already scheduled corresponding future exercise event; and determine a time for the future exercise event (362).

After generating the future exercise event, the prediction evaluation controller may provide an indication of the generated future exercise event (362) to a user. In the example of FIG. 3, the prediction evaluation controller adds the future exercise event (362) to the user's calendar as indicated in the GUI (350).

Figure 4:
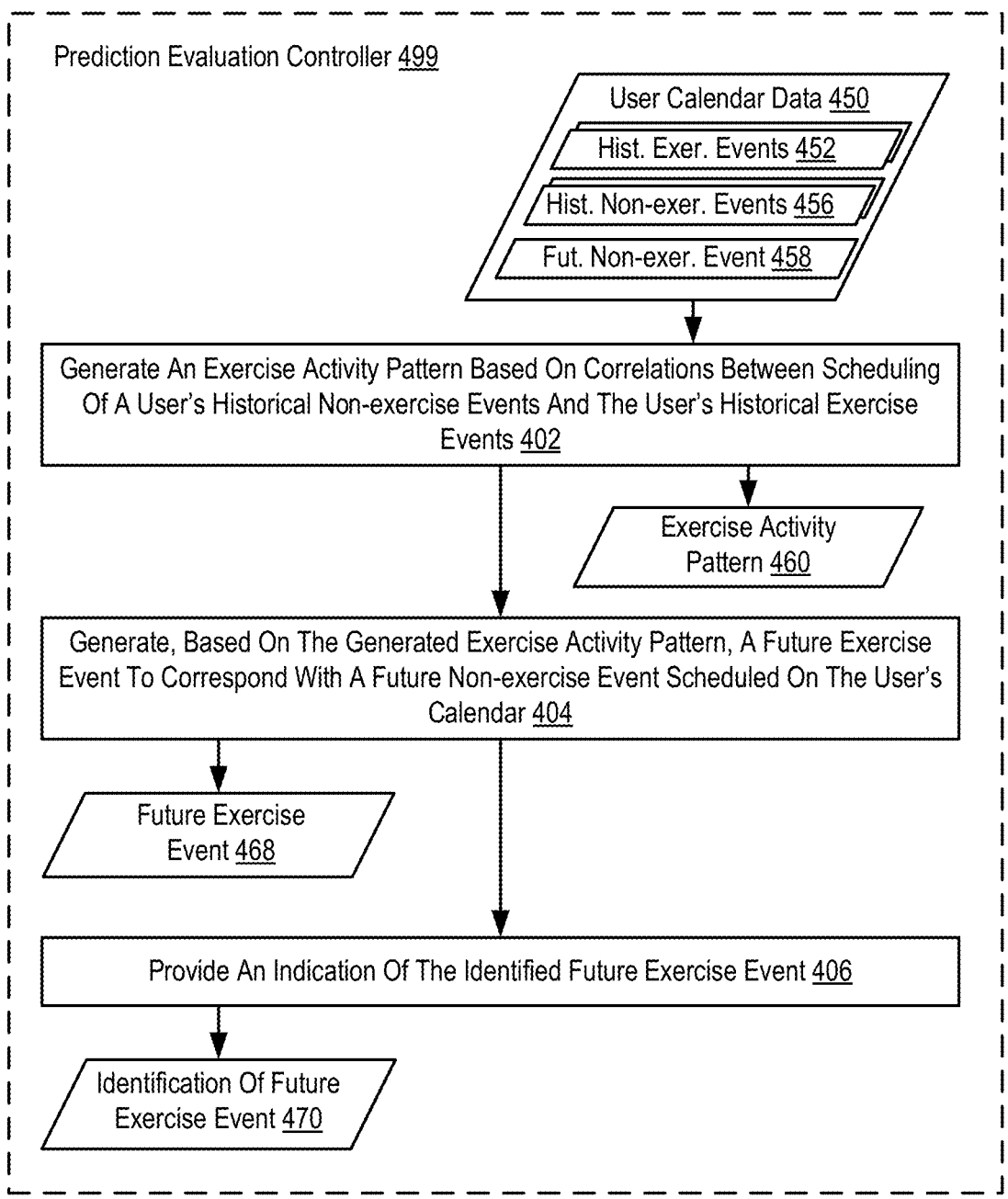

For further explanation, FIG. 4 sets forth a flow chart illustrating an example embodiment of a method for exercise behavior prediction. The method of FIG. 4 includes a prediction evaluation controller (499) generating (402) an exercise activity pattern (460) based on correlations between scheduling of a user's historical non-exercise events (456) and the user's historical exercise events (452).

A historical exercise event is a calendar event that indicates the user performed or at least was scheduled to perform an exercise activity at a particular time before the user's current time. Non-limiting examples of exercise activities include running, walking, jogging, bicycling, swimming, jumping rope, weightlifting, pushups, curl ups, yoga, elliptical moving, climbing stairs, any many other types of physical positioning that may be considered by one of skill in the art to constitute exercising. A historical exercise event may include data associated with the performance of the exercise activity. Non-limiting examples of data that may be associated with the performance of the exercise activity and that may be included in the historical exercise event include a start time of the exercise activity, a location of the exercise activity, other attendees of the exercise activity, a duration of the exercise activity, preset goals of the exercise activity, and any other information that may be useful for evaluating the historical exercise event. This data may be entered by the user or may be automatically generated based on sensor data. As part of automatically generating the data, a wearable monitoring device attached to a user may determine when the user is performing an exercise activity and may use sensor data to generate data associated with the exercise activity. For example, the wearable monitoring device (101) may determine the length of time a user is performing an exercise activity, a location the exercise activity was performed, and a physiological state of the user while the user performed the exercise activity.

A historical non-exercise event is a calendar event that indicates the user performed or at least was scheduled to perform a non-exercise activity at a particular time before the user's current time. Non-limiting examples of non-exercise activities include attending meetings, driving, flying, making telephone calls, sleeping, showering, and any other type of activity that would not be considered by one of skill in the art to constitute exercising. A historical non-exercise event may include data associated with the non-exercise activity. Non-limiting examples of data that may be associated with the performance of the non-exercise activity and that may be included in the historical non-exercise event include a start time of the non-exercise activity, a location of the non-exercise activity, other attendees of the non-exercise activity, a duration of the non-exercise activity, a type or classification of the non-exercise activity, and any other information that may be useful for evaluating the historical non-exercise event. This data may be entered by the user or may be automatically generated based on sensor data. As part of automatically generating the data, a wearable monitoring device attached to a user may determine when the user is performing a non-exercise activity and may use sensor data to generate data associated with the non-exercise activity. For example, a wearable monitoring device may determine the length of time a user is performing the non-exercise activity and the location the non-exercise activity was performed.

In a particular embodiment, to generate the data associated with the exercise event, the wearable monitoring device (101) may: determine that the user is performing an exercise activity; determine the type of exercise activity; create an exercise event in the user's calendar indicating that the user is performing an exercise activity at a particular time; and store any data collected, generated, or associated with the performance of that exercise activity. Determining that a user is performing a non-exercise activity may also be possible by examining the user's location, the user's current time, and historical calendar information to predict what non-exercise activity the user is doing. For example, a user may have a staff meeting scheduled every day at 5 P.M. at a particular location. Continuing with this example, the wearable monitoring device may schedule or prompt the user to add a staff meeting to the user's calendar in response to detecting that the user is at the particular location at 5 P.M. on a day where the staff meeting is not scheduled.

An exercise activity pattern is an indication of a repeated scheduling sequence of exercise events and non-exercise events on a user's calendar. In a particular embodiment, an exercise activity pattern consists of a rule set that indicates the repeated scheduling sequence of some combination of an exercise event and a non-exercise event. Correlations between a particular exercise event and a non-exercise event may be indicated by a variety of factors, including but not limited to: a duration of time between a non-exercise event and an exercise event; a relationship between a type or classification of a non-exercise event and an exercise event; a type of exercise activity performed during an exercise event in relation to a non-exercise event; a location of a non-exercise event and an exercise event; attendees of an exercise event or a non-exercise event; and many types of information that may be useful to indicate a pattern between an exercise event and a non-exercise event.

In summary, generating (402) an exercise activity pattern (460) based on correlations between scheduling of a user's historical non-exercise events (456) and the user's historical exercise events (452) may be carried out by retrieving user calendar data; examining the user calendar data to identify repeating sequences of exercise events and non-exercise events; and creating one or more rule sets specifying a relationship between an exercise event and a non-exercise event.

For example, an exercise activity pattern may include a rule set and data that indicates that an exercise event historically precedes a non-exercise event by a particular duration or range of time. In this example, the exercise activity pattern may indicate that a user historically goes for a run two hours before going to the airport. Another example exercise activity pattern may include a rule set that indicates an exercise event follows a particular type of non-exercise event, such as an investor meeting.

The method of FIG. 4 also includes the prediction evaluation controller (499) generating (404), based on the generated exercise activity pattern (460), a future exercise event (468) to correspond with a future non-exercise event (458) scheduled on the user's calendar. A future non-exercise event is a calendar event that indicates the user is scheduled to perform a non-exercise activity at a particular time after the current time. A future non-exercise event may include data associated with the non-exercise activity. Non-limiting examples of data that may be associated with the performance of the future non-exercise activity and that may be included in the future non-exercise event include a start time of the future non-exercise activity, a location of the future non-exercise activity, anticipated attendees of the future non-exercise activity, a scheduled duration of the non-exercise activity, a type or classification of the non-exercise activity, and any other information that may be useful for evaluating the future non-exercise event.

A future exercise event is a calendar event that indicates the user is scheduled to perform an exercise activity at a particular time after the current time. A future exercise event may include data associated with an exercise activity scheduled to be performed during the future exercise event. Non-limiting examples of data that may be associated with the future exercise activity scheduled to be performed include a start time of the future exercise activity, a location of the future exercise activity, anticipated attendees of the future exercise activity, a scheduled duration of the future exercise activity, preset goals of the future exercise activity, and any other information that may be useful for evaluating or scheduling the future exercise event.

Generating (404), based on the generated exercise activity pattern (460), a future exercise event (468) to correspond with a future non-exercise event (458) scheduled on the user's calendar may be carried out by identifying the future non-exercise event; utilizing the generated exercise activity pattern to identify a candidate future exercise event; and determining whether the user's calendar includes a future exercise event that corresponds with the candidate future exercise event. If the prediction evaluation controller (499) determines that the user's calendar does not include a future exercise event that corresponds with the candidate future exercise event, the prediction evaluation controller (499) may use the candidate future exercise event to generate the future exercise event (468).

The method of FIG. 4 also includes the prediction evaluation controller (499) providing (406) an indication (470) of the generated future exercise event (468). Providing (406) an indication (470) of the generated future exercise event (468) may be carried out by sending a recommendation message to the user suggesting a time for the future exercise event; or automatically scheduling the future exercise event. For example, the prediction evaluation controller (499) may transmit the indication (470) to another wearable monitoring device, a user's phone, or a user's computer.

Figure 5:
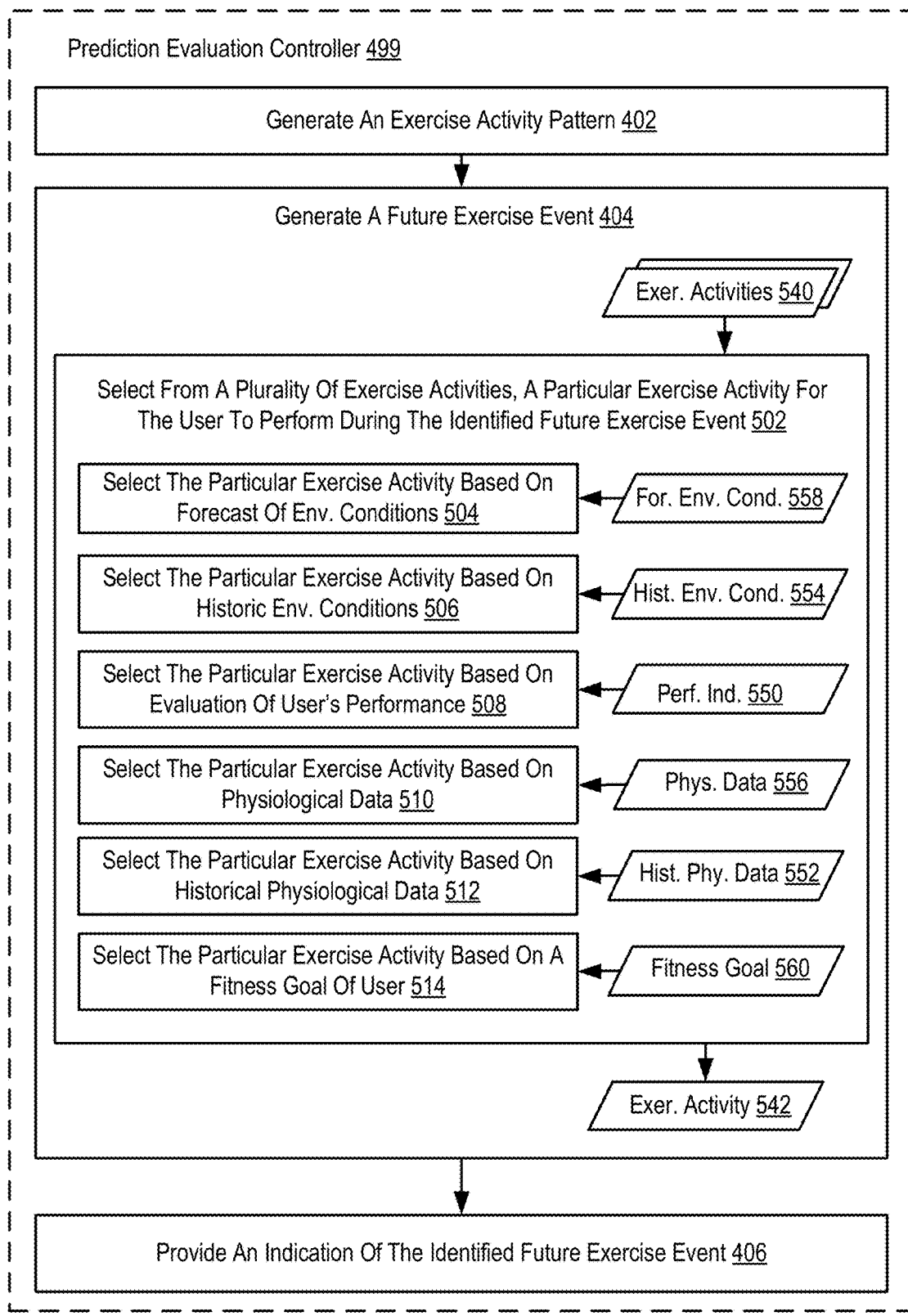

For further explanation, FIG. 5 sets forth a flow chart illustrating another example embodiment of a method for exercise behavior prediction. The method of FIG. 5 is similar to the method of FIG. 4 in that the method of FIG. 5 also includes a prediction evaluation controller (499) generating (402) an exercise activity pattern (460) based on correlations between scheduling of a user's historical non-exercise events (456) and the user's historical exercise events (452); generating (404), based on the generated exercise activity pattern (460), a future exercise event (468) to correspond with a future non-exercise event (458) scheduled on the user's calendar; and providing (406) an indication (470) of the generated future exercise event (468).

In the example of FIG. 5, generating (402) an exercise activity pattern (460) based on correlations between scheduling of a user's historical non-exercise events (456) and the user's historical exercise events (452) includes selecting (502) from a plurality of exercise activities (540), a particular exercise activity (542) for the user to perform during the generated future exercise event (468). Selecting (502) from a plurality of exercise activities (540), a particular exercise activity (542) for the user to perform during the generated future exercise event (468) may be carried out by storing a selection of a particular exercise activity within data associated with the future exercise event. For example, the prediction evaluation controller (499) may store metadata within the future exercise event indicating the selection of the particular exercise activity.

In the example of FIG. 5, selecting (502) a particular exercise activity (542) may optionally include selecting (504) the particular exercise activity (542) based on a forecast of environmental conditions (558) anticipated during the generated future exercise event (468). Environmental data may include any data indicating an environment of the user. In a particular embodiment, environmental condition data may indicate weather conditions, such as humidity level, precipitation measurements, cloud coverage, and temperature. Environmental condition data may also indicate whether the user is inside or outside. For example, during performance of an exercise activity during an exercise event, a user may provide input to a wearable monitoring device indicating that the user is indoors.

In another embodiment, environmental condition data may be measured by the wearable monitoring device. For example, the wearable monitoring device may include a sensor that monitors humidity level or temperature surrounding the wearable monitoring device. In another embodiment, the wearable monitoring device may use one or more network interfaces to receive indications of environmental conditions, such as from a weather indication application, or from a local environmental condition indication device, such as a networked humidity and temperature sensor. Forecasted environmental condition data (558) is data indicating a prediction of the environmental conditions anticipated or predicted during the future exercise event. For example, the forecasted environmental conditions may indicate a thunderstorm is predicted during the future exercise event. In this example, the prediction evaluation controller (499) may select an indoor activity, such as weightlifting at a gym for the selected exercise activity (542). Selecting (504) the particular exercise activity (542) based on a forecast of environmental condition data (558) may be carried out by receiving forecasted environmental conditions (558); and selecting an exercise activity based on a table that corresponds environmental conditions with predetermined acceptable exercise activities.

In the example of FIG. 5, selecting (502) a particular exercise activity (542) may optionally include selecting (506) the particular exercise activity (542) based on historic environmental conditions (554) during the user's performance of the one or more exercise activities during the user's historic exercise events. Historical environmental condition data is environmental condition data associated with a historical exercise event. Selecting (506) the particular exercise activity (542) based on historic environmental conditions (554) during the user's performance of the one or more exercise activities during the user's historic exercise events may be carried out by examining the types of exercise activities a user performed based on the environmental conditions present during a historical exercise event. For example, the prediction evaluation controller (499) may be determine that a user has an exercise activity pattern of choosing to swim in an indoor pool when it is raining outside and a pattern of running during exercise events when the weather is overcast. In this example, in response to a weather forecast indicating the sky will be overcast and not raining during the future exercise event, the prediction evaluation controller (499) may select as the exercise activity (542), a running exercise activity for the future exercise event (468).

In the example of FIG. 5, selecting (502) a particular exercise activity (542) may optionally include selecting (508) the particular exercise activity (542) based on an evaluation of a user's performance of one or more exercise activities during the user's historic exercise events. An evaluation of a performance of an exercise activity may include data indicating measurements associated with the performance of the exercise activity. The measurements may be entered by a user during or after the exercise event. Alternatively, the measurements may be captured or generated by a user monitoring device utilizing one or more sensor. Data that may be included in an evaluation of a user's performance of an exercise activity may include indications of distance covered in comparison to a distance goal or historical distance achievement; steps walked in comparison to a steps walked goal or historical steps walked achievement; stairs climbed in comparison to historical achievements or goals; strides taken in comparison to historical achievements or goals; a duration of the exercise activity in comparison to historical achievements or goals. Selecting (504) the particular exercise activity (542) based on an evaluation of a user's performance of one or more exercise activities during the user's historic exercise events may be carried out by using the data in the evaluation to rank and sort possible exercise activities based on the user's past performance; and selecting the exercise activity based on the ranking of the sorted possible exercise activities.

For example, evaluation of performance indicators (550) may indicate that the user typically fails to complete scheduled five mile runs but typically does complete scheduled bicycle rides. In this example, the prediction evaluation controller (499) may rank a bicycle exercise activity higher than a running exercise activity; and therefore may select a bicycle exercise activity more often than selecting a running exercise activity.

In the example of FIG. 5, selecting (502) a particular exercise activity (542) may optionally include selecting (510) the particular exercise activity (542) based on current physiological data (556) indicating at least one vital sign of the user. Physiological data is data generated from sensors monitoring one or more vital signs of a user. Non-limiting examples of physiological data include hydration measurements, heart rate, oxygen saturation, temperature, muscle contractions, blood pressure, and any other types of measurements indicating a vital sign of a person. Selecting (510) the particular exercise activity (542) further based on current physiological data (556) may be carried out by comparing the physiological data (556) to a threshold and recommending an exercise activity that may lower a value of the physiological data to below the threshold. For example, the physiological data may indicate a hydration level of a user. In this example, the prediction evaluation controller (499) may determine if the hydration level of the user is below a hydration level threshold and recommend a specific type of exercise activity if the user's hydration level is below the hydration level threshold. The prediction evaluation controller (499) may also include a specific hydration level threshold for each particular exercise activity.

In the example of FIG. 5, selecting (502) a particular exercise activity (542) may optionally include selecting (512) the particular exercise activity (542) based on historic physiological data (552) indicating at least one vital sign of the user during the user's performance of the one or more exercise activities during the user's historic exercise events. Selecting (512) the particular exercise activity (542) based on historic physiological data (552) indicating at least one vital sign of the user during the user's performance of the one or more exercise activities during the user's historic exercise events may be carried out by evaluating the user's performance of an exercise activity in view of the physiological state of the user while performing the exercise activity. For example, the prediction evaluation controller (499) may evaluate a user's performance during a scheduled five mile run as part of the process of selecting an exercise activity for the future exercise event. In this example, if the user fails to complete the five mile run, the prediction evaluation controller (499) may also examine the physiological state of the user to determine if there were other factors that may have impaired the user's ability to complete the run. Continuing with this example, the prediction evaluation controller (499) may determine that the user is typically severely dehydrated during exercise events having a five mile run planned as the exercise activity. In this example, instead of not scheduling five mile runs for the selected exercise activities of future exercise events, the prediction evaluation controller (499) may select a five mile run along with provide a physiological improvement recommendation that the user get hydrated before the run. Generating and providing a physiological improvement recommendation will be explained in greater detail in the description of FIG. 7.

In the example of FIG. 5, selecting (502) a particular exercise activity (542) may optionally include selecting (514) the particular exercise activity (542) based on a fitness goal (560) of the user. An identified fitness goal of a user is any indication of the fitness goal a user is trying to achieve. Non-limiting examples of fitness goals include losing weight, gaining weight, building muscle, burning fat, building cardio endurance, building high intensity short interval cardio endurance, building long distance cardio endurance, or any indication of a change or measure that the user is interesting in achieving. For example, a user may indicate that the user's fitness goal is to build muscle. Continuing with this example, the prediction evaluation controller (199) may select a weightlifting exercise activity as the exercise activity (542). Selecting (514) the particular exercise activity (542) based on a fitness goal (560) of the user may be carried out by using the fitness goal of the user to identify one or more exercise activities that will help a user achieve the fitness goal.

Figure 6:
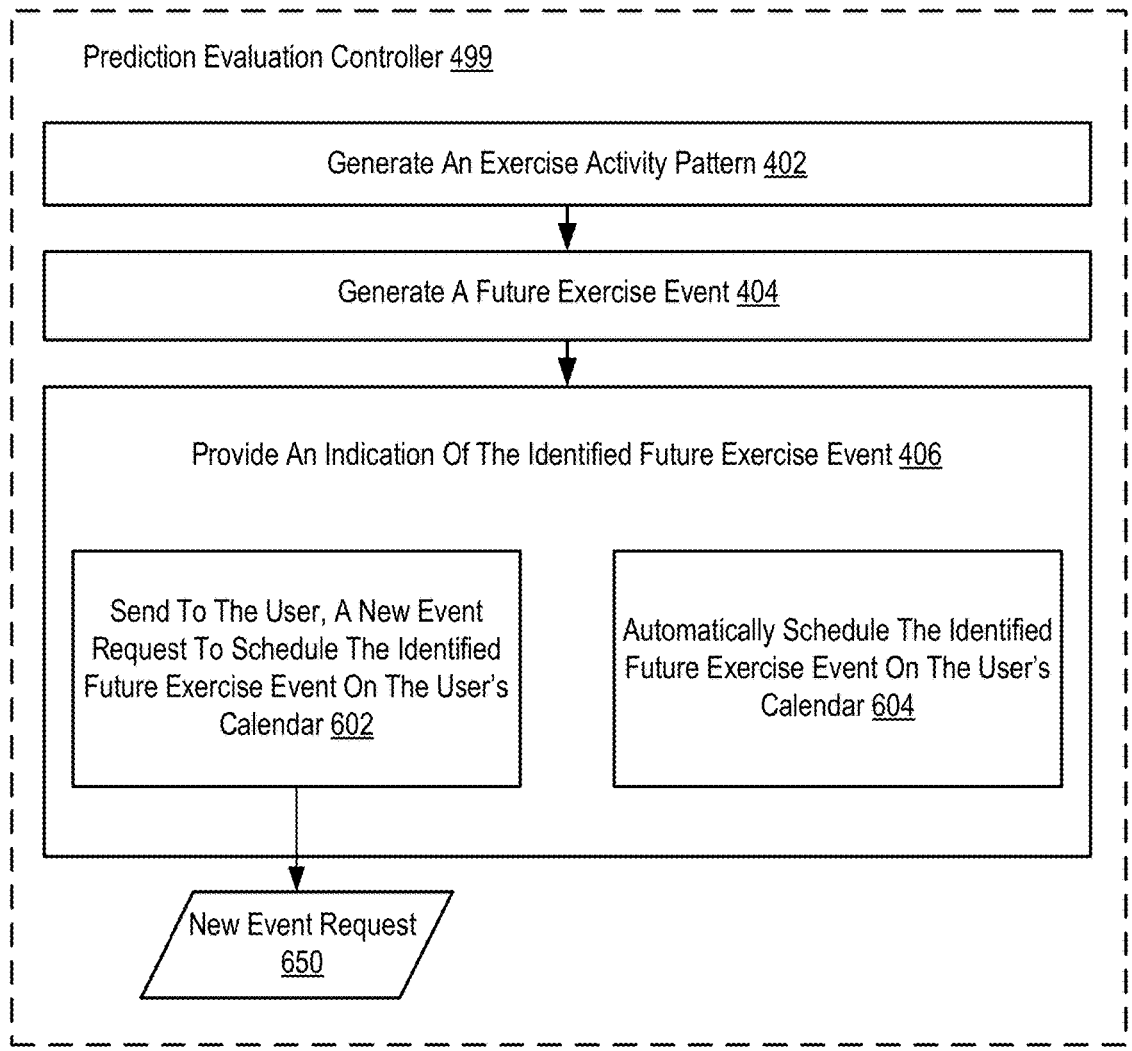

For further explanation, FIG. 6 sets forth a flow chart illustrating another example embodiment of a method for exercise behavior prediction. The method of FIG. 6 is similar to the method of FIG. 4 in that the method of FIG. 6 also includes a prediction evaluation controller (499) generating (402) an exercise activity pattern (460) based on correlations between scheduling of a user's historical non-exercise events (456) and the user's historical exercise events (452); generating (404), based on the generated exercise activity pattern (460), a future exercise event (468) to correspond with a future non-exercise event (458) scheduled on the user's calendar; and providing (406) an indication (470) of the generated future exercise event (468).

In the example of FIG. 6, providing (406) an indication (470) of the generated future exercise event (468) optionally includes sending (602) to the user, a new event request (650) to schedule the generated future exercise event (468) on the user's calendar. Sending (602) to the user, a new event request (650) to schedule the generated future exercise event (468) on the user's calendar may be carried out by generating a calendar message that includes data associated with the future exercise event.

In the example of FIG. 6, providing (406) an indication (470) of the generated future exercise event (468) also optionally includes automatically scheduling (604) the generated future exercise event (468) on the user's calendar. Automatically scheduling (604) the generated future exercise event (468) on the user's calendar may be carried out by coordinating with a program that controls the user's calendar to add the generated future exercise event to the calendar.

Figure 7:
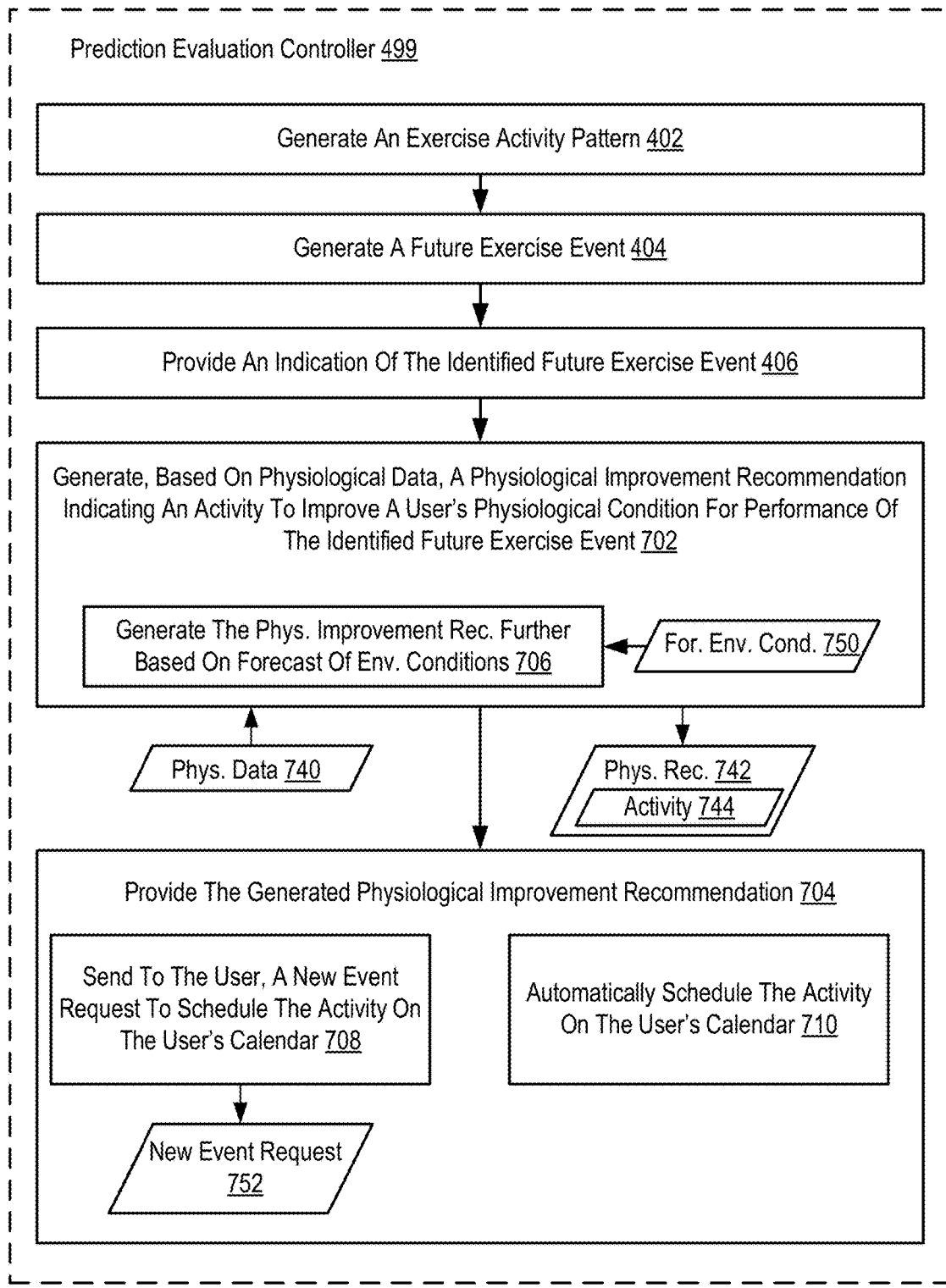

For further explanation, FIG. 7 sets forth a flow chart illustrating another example embodiment of a method for exercise behavior prediction. The method of FIG. 7 is similar to the method of FIG. 4 in that the method of FIG. 7 also includes a prediction evaluation controller (499) generating (402) an exercise activity pattern (460) based on correlations between scheduling of a user's historical non-exercise events (456) and the user's historical exercise events (452); generating (404), based on the generated exercise activity pattern (460), a future exercise event (468) to correspond with a future non-exercise event (458) scheduled on the user's calendar; and providing (406) an indication (470) of the generated future exercise event (468).

The method of FIG. 7 also includes the prediction evaluation controller (499) generating (702), based on physiological data (740) indicating at least one vital sign of the user, a physiological improvement recommendation (742) indicating an activity (744) to improve a user's physiological condition for performance of the generated future exercise event (468). A physiological improvement recommendation indicates an activity predetermined to improve one or more aspects of the user's physiological state. For example, if a user is dehydrated, the prediction evaluation controller (499) may generate a physiological improvement recommendation suggesting a hydration activity, such as drinking water. Generating (702) a physiological improvement recommendation (742) may be carried out by examining a user's physiological state during a performance of an exercise activity; identifying one or more physiological parameters that was outside of an acceptable range during the particular exercise activity; and generating a physiological improvement recommendation to correspond with the future exercise event if the particular exercise activity is scheduled during the future exercise event. For example, if the prediction evaluation controller (499) determines that a user typically is dehydrated during a running exercise activity, the prediction evaluation controller (499) may suggest a hydration activity at some point before a future exercise event that includes running as the exercise activity. Non-limiting examples of other physiological improvement recommendations include indicating a cool down activity in response to the user being outside for too long or having a body temperature that is above a threshold; indicating a warm up activity in response to the user being sedentary for a length of time; indicating the user eat carbohydrates, such as before a cardio intensive exercise activity; indicating the user eat protein before or after a weightlifting exercise activity; indicating the user increase oxygen saturation, such as being doing an exercise activity such as skiing or rock climbing; and many others as will occur to those of skill in the art.

Generating (702) a physiological improvement recommendation (742) may also be carried out by examining a table that associates exercise activities with predefined ranges of acceptable physiological parameters; determining whether the user's current physiological state is outside of the acceptable physiological parameters associated with an exercise activity scheduled during a future exercise event; and identifying one or more physiological improvement activities to change the user's physiological state into accordance with the acceptable physiological parameters. For example, the prediction evaluation controller (499) may determine that a user should have an optimal hydration level before starting a run. In this example, the prediction evaluation controller (499) may generate a physiological improvement recommendation that suggests a hydration activity a couple of hours before going running if the prediction evaluation controller determines the user's hydration level is below the optimal level. The duration between the future exercise event and the activity in the physiological improvement recommendation may depend upon the type of activity recommended in the physiological improvement recommendation.

In the example of FIG. 7, generating (702) a physiological improvement recommendation (742) may optionally include generating (706) a physiological improvement recommendation (742) further based on a forecast of environmental conditions (750) anticipated during the generated future exercise event (468). Generating (706) a physiological improvement recommendation (742) further based on a forecast of environmental conditions (750) anticipated during the generated future exercise event (468) may be carried out by changing one or more parameters of the physiological improvement recommendation based on the expected weather conditions for a future exercise event. For example, the prediction evaluation controller may generate a physiological improvement recommendation based on the forecasted environmental conditions indicating the weather will have a particular humidity level and temperature level. In this example, the physiological improvement recommendation may recommend the user start an exercise activity with higher hydration levels as the humidity level and temperature level forecasted for the exercise event increase.

The method of FIG. 7 also includes the prediction evaluation controller (499) providing (704) the generated physiological improvement recommendation (740). Providing (704) the generated physiological improvement recommendation (740) may be carried out by displaying a message that indicates the physiological improvement recommendation.

In the example of FIG. 7, providing (704) the generated physiological improvement recommendation (740) optionally includes sending (708) to the user, a new event request (752) to schedule the activity (744) indicated in the identified physiological improvement recommendation (742). Sending (708) to the user, a new event request (752) to schedule the activity (744) indicated in the identified physiological improvement recommendation (742) may be carried out by transmitting a message asking the user if the user wants to schedule the activity suggested in the physiological improvement recommendation.

In the example of FIG. 7, providing (704) the generated physiological improvement recommendation (740) optionally includes automatically scheduling (710) the activity (744) indicated in the identified physiological improvement recommendation (742). Automatically scheduling (710) the activity (744) indicated in the identified physiological improvement recommendation (742) may be carried out by coordinating with a program that controls the user's calendar to add a physiological improvement activity indicated in the physiological improvement recommendation.

Figure 8:
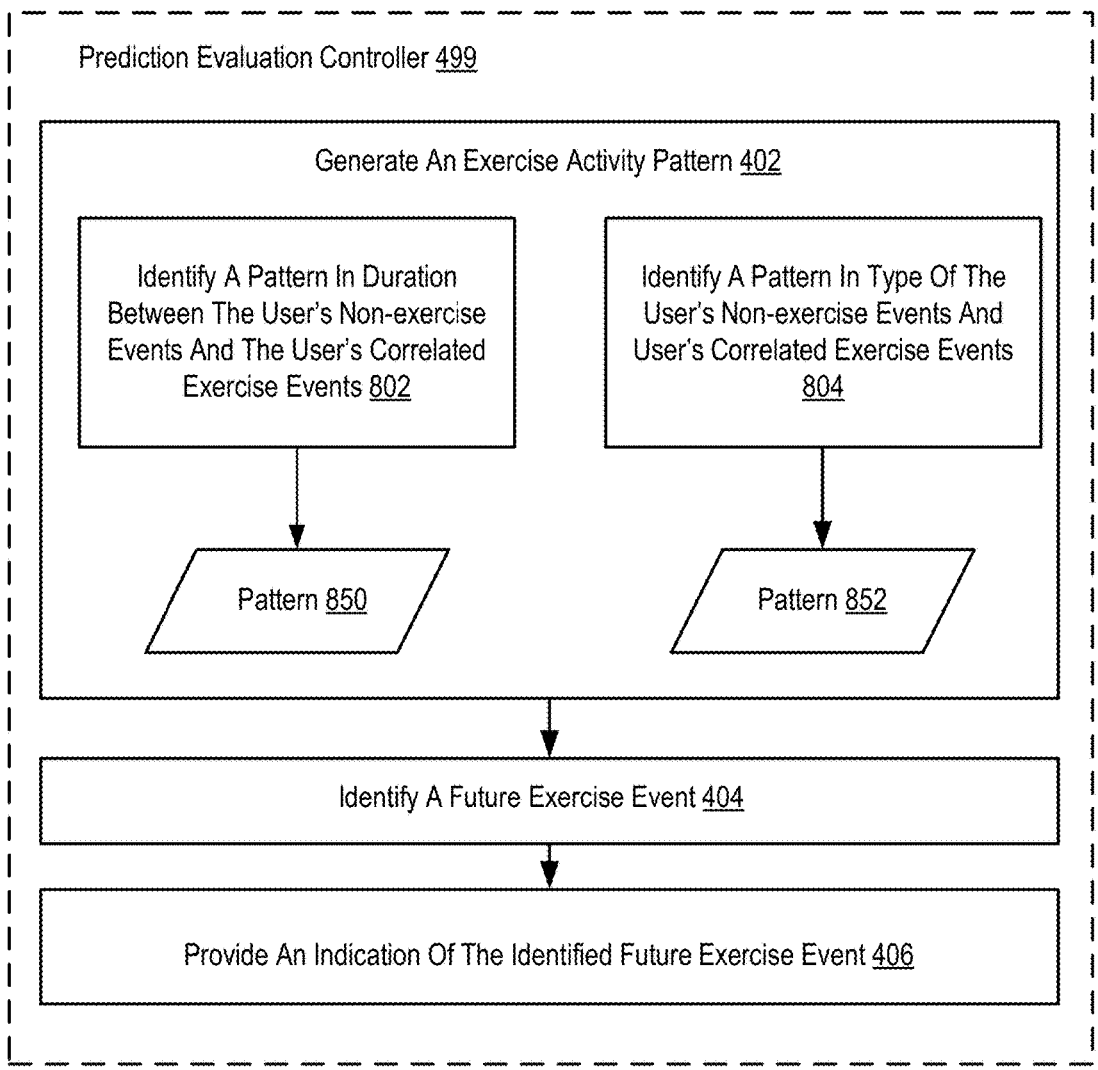

For further explanation, FIG. 8 sets forth a flow chart illustrating another example embodiment of a method for exercise behavior prediction. The method of FIG. 8 is similar to the method of FIG. 4 in that the method of FIG. 7 also includes a prediction evaluation controller (499) generating (402) an exercise activity pattern (460) based on correlations between scheduling of a user's historical non-exercise events (456) and the user's historical exercise events (452); generating (404), based on the generated exercise activity pattern (460), a future exercise event (468) to correspond with a future non-exercise event (458) scheduled on the user's calendar; and providing (406) an indication (470) of the generated future exercise event (468).

In the example of FIG. 8, generating (404), based on the generated exercise activity pattern (460), a future exercise event (468) to correspond with a future non-exercise event (458) scheduled on the user's calendar optionally includes identifying (802) a pattern (850) in the duration between the user's non-exercise events and the user's correlated exercise events. Identifying (802) a pattern (850) in the duration between the user's non-exercise events and the user's correlated exercise events may be carried out by retrieving user calendar data; examining the user calendar data to identify repeating durations between particular exercise events and non-exercise events; and creating one or more rule sets specifying a duration relationship between an exercise event and a non-exercise event.

For example, an exercise activity pattern may include a rule set and data that indicates that an exercise event historically precedes a non-exercise event by a particular duration or range of time. In this example, the exercise activity pattern may indicate that a user historically goes for a run two hours before going to the airport.

In the example of FIG. 8, generating (404), based on the generated exercise activity pattern (460), a future exercise event (468) to correspond with a future non-exercise event (458) scheduled on the user's calendar optionally includes identifying (804) a pattern (852) in type of the user's non-exercise events and the user's correlated exercise events. Identifying (804) a pattern (852) in type of the user's non-exercise events and the user's correlated exercise events may be carried out by retrieving user calendar data; examining the user calendar data to identify repeating sequences between particular types of exercise activities during exercise events and types of non-exercise events; and creating one or more rule sets specifying a relationship between the particular type of exercise activity and a type of non-exercise event. For example, the prediction evaluation controller (499) may generate an exercise activity pattern that includes a rule set that indicates an exercise event proceeds or follows a particular type of non-exercise event, such as an investor meeting. As another example, the prediction evaluation controller (499) may generate an exercise activity pattern that includes a rules set that indicates a particular type of exercise activity proceeds or follows a particular type of non-exercise event.

Figure 9:
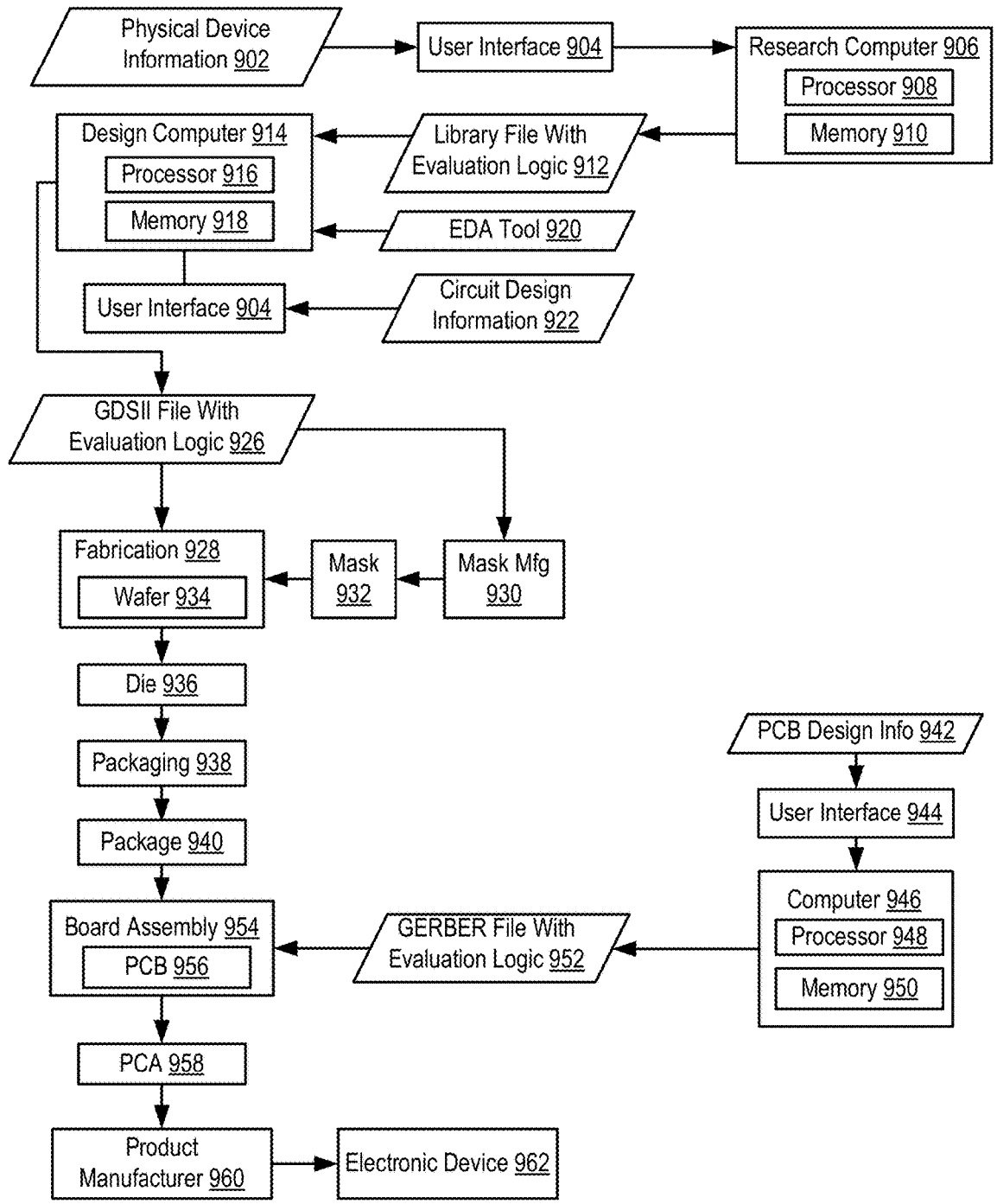

For further explanation, FIG. 9 sets forth a data flow diagram illustrating a manufacturing process (900) for a device that includes a prediction evaluation controller. Physical device information (902 is received at the manufacturing process (900), such as at a research computer (906). The physical device information (902) may include design information representing at least one physical property of a semiconductor device, such as a device that includes the prediction evaluation controller (199) of FIG. 1 (e.g., the wearable monitoring device (101) of FIG. 1). For example, the physical device information (902) may include physical parameters, material characteristics, and structure information that is entered via a user interface (904) coupled to the research computer (906). The research computer (906) includes a processor (908), such as one or more processing cores, coupled to a computer readable medium such as a memory (910). The memory (910) may store computer readable instructions that are executable to cause the processor (908) to transform the physical device information (902) to comply with a file format and to generate a library file (912) containing evaluation logic for exercise behavior prediction.

In a particular embodiment, the library file (912) includes at least one data file including the transformed design information. For example, the library file (912) may include a library of semiconductor devices including a device that includes the prediction evaluation controller (199) of FIG. 1 (e.g., the wearable monitoring device (101) of FIG. 1) that is provided to use with an electronic design automation (EDA) tool (920).

The library file (912) may be used in conjunction with the EDA tool (920) at a design computer (914) including a processor (916), such as one or more processing cores, coupled to a memory (918). The EDA tool (920) may be stored as processor executable instructions at the memory (918) to enable a user of the design computer (914) to design a circuit including a device that includes the prediction evaluation controller (199) of FIG. 1 (e.g., the wearable monitoring device (101) of FIG. 1) of the library file (912). For example, a user of the design computer (914) may enter circuit design information (922) via a user interface (924) coupled to the design computer (914). The circuit design information (922) may include design information representing at least one physical property of a semiconductor device, such as a device that includes the prediction evaluation controller (199) of FIG. 1 (e.g., the wearable monitoring device (101) of FIG. 1). To illustrate, the circuit design property may include identification of particular circuits and relationships to other elements in a circuit design, positioning information, feature size information, interconnection information, or other information representing a physical property of a semiconductor device.

The design computer (914) may be configured to transform the design information, including the circuit design information (922), to comply with a file format. To illustrate, the file formation may include a database binary file format representing planar geometric shapes, text labels, and other information about a circuit layout in a hierarchical format, such as a Graphic Data System (GDSII) file format. The design computer (914) may be configured to generate a data file including the transformed design information, such as a GDSII file (926) that includes information describing a device that includes evaluation logic used by the prediction evaluation controller (199) of FIG. 1 (e.g., the wearable monitoring device (101) of FIG. 1) for exercise behavior prediction in addition to other circuits or information. To illustrate, the data file may include information corresponding to a system-on-chip (SOC) that includes a device that includes the prediction evaluation controller (199) of FIG. 1 (e.g., the wearable monitoring device (101) of FIG. 1) and that also includes additional electronic circuits and components within the SOC.

The GDSII file (926) may be received at a fabrication process (928) to manufacture a device that includes the prediction evaluation controller (199) of FIG. 1 (e.g., the wearable monitoring device (101) of FIG. 1) according to transformed information in the GDSII file (926). For example, a device manufacture process may include providing the GDSII file (926) to a mask manufacturer (930) to create one or more masks, such as masks to be used with photolithography processing, illustrated as a representative mask (932). The mask (932) may be used during the fabrication process to generate one or more wafers (934), which may be tested and separated into dies, such as a representative die (936). The die (936) includes a circuit including a device that includes the prediction evaluation controller (199) of FIG. 1 (e.g., the wearable monitoring device (101) of FIG. 1).

The die (936) may be provided to a packaging process (938) where the die (936) is incorporated into a representative package (940). For example, the package (940) may include the single die (936) or multiple dies, such as a system-in-package (SiP) arrangement. The package (940) may be configured to conform to one or more standards or specifications, such as Joint Electron Device Engineering Council (JEDEC) standards.

Information regarding the package (940) may be distributed to various product designers, such as via a component library stored at a computer (946). The computer (946) may include a processor (948), such as one or more processing cores, coupled to a memory (950). A printed circuit board (PCB) tool may be stored as processor executable instructions at the memory (950) to process PCB design information (942) received from a user of the computer (946) via a user interface (944). The PCB design information (942) may include physical positioning information of a packaged semiconductor device on a circuit board, the packaged semiconductor device corresponding to the package (940) including a device that includes the prediction evaluation controller (199) of FIG. 1 (e.g., the wearable monitoring device (101) of FIG. 1).

The computer (946) may be configured to transform the PCB design information (942) to generate a data file, such as a GERBER file (952) with data that includes physical positioning information of a packaged semiconductor device on a circuit board, as well as layout of electrical connections such as traces and vias, where the packaged semiconductor device corresponds to the package (940) including the prediction evaluation controller (199) of FIG. 1. In other embodiments, the data file generated by the transformed PCB design information may have a format other than a GERBER format.

The GERBER file (952) may be received at a board assembly process (954) and used to create PCBs, such as a representative PCB (956), manufactured in accordance with the design information stored within the GERBER file (952). For example, the GERBER file (952) may be uploaded to one or more machines to perform various steps of a PCB production process. The PCB (956) may be populated with electronic components including the package (940) to form a representative printed circuit assembly (PCA) (958).

The PCA (958) may be received at a product manufacture process (960) and integrated into one or more electronic devices, such as a first representative electronic device (962) and a second representative electronic device (964). As an illustrative, non-limiting example, the first representative electronic device (962), the second representative electronic device (964), or both, may be selected from the group of a set top box, a music player, a video player, an entertainment unit, a navigation device, a communications device, a personal digital assistant (PDA), a fixed location data unit, and a computer, into which the at least one controllable energy consuming module is integrated. As another illustrative, non-limiting example, one or more of the electronic devices (962) and (964) may be remote units such as mobile phones, hand-held personal communication systems (PCS) units, portable data units such as personal data assistants, global positioning system (GPS) enabled devices, navigation devices, fixed location data units such as meter reading equipment, or any other device that stores or retrieves data or computer instructions, or any combination thereof. Although FIG. 8 illustrates remote units according to teachings of the disclosure, the disclosure is not limited to these exemplary illustrated units. Embodiments of the disclosure may be suitably employed in any device which includes active integrated circuitry including memory and on-chip circuitry.

A device that includes the prediction evaluation controller (199) of FIG. 1 may be fabricated, processed, and incorporated into an electronic device, as described in the illustrative process (900). One or more aspects of the embodiments disclosed with respect to FIGS. 1-7 may be included at various processing stages, such as within the library file (912), the GDSII file (926), and the GERBER file (952), as well as stored at the memory (910) of the research computer (906), the memory (918) of the design computer (914), the memory (950) of the computer (946), the memory of one or more other computers or processors (not shown) used at the various stages, such as at the board assembly process (954), and also incorporated into one or more other physical embodiments such as the mask (932), the die (936), the package (940), the PCA (958), other products such as prototype circuits or devices (not shown), or any combination thereof. For example, the GDSII file (926) or the fabrication process (928) can include a computer readable tangible medium storing instructions executable by a computer, the instructions including instructions that are executed by the computer to perform the methods of FIGS. 3-7, or any combination thereof. Although various representative stages of production from a physical device design to a final product are depicted, in other embodiments fewer stages may be used or additional stages may be included.

Similarly, the process (900) may be performed by a single entity, or by one or more entities performing various stages of the process (900).

Those of skill would further appreciate that the various illustrative logical blocks, configurations, modules, circuits, and method steps described in connection with the embodiments disclosed herein may be implemented as electronic hardware, computer software executed by a processing unit, or combinations of both. Various illustrative components, blocks, configurations, modules, circuits, and steps have been described above generally in terms of their functionality. Whether such functionality is implemented as hardware or executable processing instructions depends on the particular application and design constraints imposed on the overall system. Skilled artisans may implement the described functionality in varying ways with each particular application, but such implementation decisions should not be interpreted as causing a departure from the scope of the present disclosure.

The steps of a method or algorithm described in connection with the embodiments disclosed herein may be embodied directly in hardware, in a software module executed by a processor, or in a combination of the two. A software module may reside in random access memory (RAM), a magnetoresistive random access memory (MRAM), a spin-torque-transfer MRAM (STT-MRAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of storage medium known in the art. An exemplary storage medium is coupled to the processor such that the processor can read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor and the storage medium may reside as discrete components in a computing device or user terminal.

The previous description of the disclosed embodiments is provided to enable any person skilled in the art to make or use the disclosed embodiments. Various modifications to these embodiments will be readily apparent to those skilled in the art, and the principles defined herein may be applied to other embodiments without departing from the scope of the disclosure. Thus, the present disclosure is not intended to be limited to the embodiments shown herein but is to be accorded the widest scope possible consistent with the principles and novel features as defined by the following claims.

What is claimed is:

1. A method of exercise behavior prediction, the method comprising:
    receiving, by a computing system via one or more sensors associated therewith, activity data of a user;
    inferring, by the computing system, that the user is performing an exercise event based on the activity data;
    adding, by the computing system, the exercise event to a calendar application associated with the user;
    identifying, by the computing system, a plurality of historical calendar entries contained in the calendar application, wherein the plurality of historical calendar entries comprises one or more historical non-exercise events and one or more historical exercise events, wherein the one or more historical exercise events comprises the exercise event inferred by the computing system based on the activity data;

generating, by the computing system using a prediction evaluation controller, an exercise activity pattern based on identifying correlations between the one or more historical non-exercise events and the one or more historical exercise events;

identifying, by the computing system, a future non-exercise event in the calendar application;

based on identifying the future non-exercise event, generating, by the computing system via the prediction evaluation controller, a future exercise event to correspond with a future non-exercise event based on the generated exercise activity pattern and the future non-exercise event; and providing, by the computing system, an indication of the future exercise event to the user.

2. The method of claim 1 wherein generating a future exercise event includes selecting from a plurality of exercise activities, a particular exercise activity for the user to perform during the generated future exercise event.

3. The method of claim 2 wherein selecting the particular exercise activity is based on an evaluation of a user's performance of one or more exercise activities during the user's historic exercise events.

4. The method of claim 2 wherein selecting the particular exercise activity is based on historic physiological data indicating at least one vital sign of the user during the user's performance of the one or more exercise activities during the user's historic exercise events.

5. The method of claim 2 wherein selecting the particular exercise activity is based on historic environmental conditions during the user's performance of the one or more exercise activities during the user's historic exercise events.

6. The method of claim 2 wherein selecting the particular exercise activity is based on current physiological data indicating at least one vital sign of the user.

7. The method of claim 2 wherein selecting the particular exercise activity is based on a forecast of environmental conditions anticipated during the generated future exercise event.

8. The method of claim 2 wherein selecting the particular exercise activity is based on a fitness goal of the user.

9. The method of claim 1 wherein providing the indication of the generated future exercise event includes sending to the user, a new event request to schedule the generated future exercise event on the user's calendar.

10. The method of claim 1 wherein providing the indication of the generated future exercise event includes automatically scheduling the generated future exercise event on the user's calendar.

11. The method of claim 1 further comprising:

generating, based on physiological data indicating at least one vital sign of the user, by the prediction evaluation controller, a physiological improvement recommendation indicating an activity to improve a user's physiological condition for performance of the generated future exercise event; and providing, by the prediction evaluation controller, the generated physiological improvement recommendation.

12. The method of claim 11 wherein generating the physiological improvement recommendation is further based on a forecast of environmental conditions anticipated during the generated future exercise event.

13. The method of claim 11 wherein providing the generated physiological improvement recommendation includes sending to the user, a new event request to schedule the activity indicated in the identified physiological improvement recommendation.

14. The method of claim 11 wherein providing the generated physiological improvement recommendation includes automatically scheduling the activity indicated in the identified physiological improvement recommendation.

15. The method of claim 1 wherein generating an exercise activity pattern based on correlations between scheduling of a user's historical non-exercise events and the user's historical exercise events includes identifying a pattern in the duration between the user's non-exercise events and the user's correlated exercise events.

16. The method of claim 1 wherein generating an exercise activity pattern based on correlations between scheduling of a historical user's non-exercise events and the user's historical exercise events includes identifying a pattern in type of the user's non-exercise events and the user's correlated exercise events.

17. An apparatus for exercise behavior prediction, the apparatus comprising a computer processor and computer memory operatively coupled to the computer processor, the computer memory having disposed within it computer program instructions that, when executed by the computer processor, cause the apparatus to carry out the steps of:

receiving, by the computer processor via one or more sensors associated therewith, activity data of a user;

inferring, by the computer processor, that the user is performing an exercise event based on the activity data;

adding, by the computer processor, the exercise event to a calendar application associated with the user;

identifying, by the computer processor, a plurality of historical calendar entries contained in the calendar application, wherein the plurality of historical calendar entries comprises one or more historical non-exercise events and one or more historical exercise events, wherein the one or more historical exercise events comprises the exercise event inferred by the computing system based on the activity data;

generating, by the computer processor via a prediction evaluation controller, an exercise activity pattern based on identifying correlations between the one or more historical non-exercise events and the one or more historical exercise events;

identifying, by the computer processor, a future non-exercise event in the calendar application;

based on identifying the future non-exercise event, generating, by the computer processor via the prediction evaluation controller, a future exercise event to correspond with a future non-exercise events based on the generated exercise activity pattern and the future non-exercise event; and providing, by the computer processor, an indication of the generated future exercise event to the user.

18. The apparatus of claim 17 further comprising computer program instructions that, when executed by the computer processor, cause the apparatus to carry out the steps of:

generating, based on physiological data indicating at least one vital sign of the user, by the prediction evaluation controller, a physiological improvement recommendation indicating an activity to improve a user's physiological condition for performance of the generated future exercise event; and providing, by the prediction evaluation controller, the generated physiological improvement recommendation.

19. A non-transitory computer readable medium comprising one or more sequences of instructions, which, when executed by one or more processors, cause a computing system to perform operations, comprising:
- receiving, by a computing system via one or more sensors associated therewith, activity data of a user;
- inferring, by the computing system, that the user is performing an exercise event based on the activity data;
- adding, by the computing system, the exercise event to a calendar application associated with the user;
- identifying, by the computing system, a plurality of historical calendar entries contained in the calendar application, wherein the plurality of historical calendar entries comprises one or more historical non-exercise events and one or more historical exercise events, wherein the one or more historical exercise events comprises the exercise event inferred by the computing system based on the activity data;
- generating, by the computing system via a prediction evaluation controller, an exercise activity pattern based on identifying correlations between the one or more historical non-exercise events and the one or more historical exercise events;
- identifying, by the computing system, a future non-exercise event in the calendar application;
- based on identifying the future non-exercise event, generating, by the computing system via the prediction evaluation controller, a future exercise event to correspond with the future non-exercise events based on the generated exercise activity pattern and the future non-exercise event; and
- providing, by the computing system, an indication of the future exercise event to the user.

20. The non-transitory computer readable medium of claim 19 wherein the instructions are executable by a processor integrated into a device selected from the group consisting of a navigation device, a communications device, a personal digital assistant (PDA), a fixed location data unit, and a computer.

* * * * *